United States Patent
Purkayastha et al.

(10) Patent No.: US 10,780,170 B2
(45) Date of Patent: Sep. 22, 2020

(54) STEVIA EXTRACT CONTAINING SELECTED STEVIOL GLYCOSIDES AS FLAVOR, SALTY AND SWEETNESS PROFILE MODIFIER

(71) Applicant: PureCircle USA Inc., Oak Brook, IL (US)

(72) Inventors: Siddhartha Purkayastha, Chicago, IL (US); Marcia Petit, Chicago, IL (US)

(73) Assignee: PureCircle Sdn Bhd, Kuala Lumpur (MY)

(*) Notice: Subject to any disclaimer, the term of this patent is extended or adjusted under 35 U.S.C. 154(b) by 0 days.

(21) Appl. No.: 14/896,022

(22) PCT Filed: Jun. 9, 2014

(86) PCT No.: PCT/US2014/041548
§ 371 (c)(1),
(2) Date: Dec. 4, 2015

(87) PCT Pub. No.: WO2014/197898
PCT Pub. Date: Dec. 11, 2014

(65) Prior Publication Data
US 2016/0128371 A1   May 12, 2016

Related U.S. Application Data

(60) Provisional application No. 61/832,451, filed on Jun. 7, 2013, provisional application No. 61/942,331, filed on Feb. 20, 2014.

(51) Int. Cl.
| | | |
|---|---|---|
| *A61K 47/36* | (2006.01) | |
| *A23G 3/34* | (2006.01) | |
| *A23L 27/30* | (2016.01) | |
| *A23L 33/105* | (2016.01) | |
| *A23L 27/00* | (2016.01) | |
| *A23L 2/60* | (2006.01) | |

(52) U.S. Cl.
CPC .............. *A61K 47/36* (2013.01); *A23G 3/346* (2013.01); *A23L 2/60* (2013.01); *A23L 27/33* (2016.08); *A23L 27/36* (2016.08); *A23L 27/88* (2016.08); *A23L 33/105* (2016.08); *A23V 2002/00* (2013.01)

(58) Field of Classification Search
CPC . A23G 3/346; A23L 2/60; A23L 27/33; A23L 27/36; A23L 27/88; A23L 33/105; A23L 1/2366; A23V 2002/00; A61K 47/36
See application file for complete search history.

(56) References Cited

U.S. PATENT DOCUMENTS

| | | | |
|---|---|---|---|
| 2,500,173 A | 3/1950 | Gisvold | |
| 2,615,015 A | 10/1952 | Wilson | |
| 3,723,410 A | 3/1973 | Persinos | |
| 4,082,858 A | 4/1978 | Morita | |
| 4,112,218 A | 9/1978 | Inoue | |
| 4,171,430 A | 10/1979 | Matsushita | |
| 4,219,571 A | 8/1980 | Miyake | |
| 4,361,697 A | 11/1982 | Dobberstein | |
| 4,454,290 A | 6/1984 | Dubois | |
| 4,590,160 A | 5/1986 | Nishihashi | |
| 4,599,403 A | 7/1986 | Kumar | |
| 4,612,942 A | † 9/1986 | Dobberstein | |
| 4,657,638 A | 4/1987 | le Grand | |
| 4,892,938 A | 1/1990 | Giovanetto | |
| 4,915,969 A | 4/1990 | Beyts | |
| 4,917,916 A | 4/1990 | Hirao | |
| 5,112,610 A | 5/1992 | Kienle | |
| 5,576,042 A | 11/1996 | Fuisz | |
| 5,779,805 A | 7/1998 | Morano | |
| 5,830,523 A | 11/1998 | Takaichi | |
| 5,962,678 A | 10/1999 | Payzant | |
| 5,972,120 A | 10/1999 | Kutowy | |
| 6,031,157 A | 2/2000 | Morita | |
| 6,080,561 A | 6/2000 | Morita | |
| 6,204,377 B1 | 3/2001 | Nishimoto | |
| 6,228,996 B1 | 5/2001 | Zhou | |
| 6,318,157 B1 | 11/2001 | Corso | |
| 6,706,304 B1 | 3/2004 | Ishida | |
| 7,807,206 B2 | 10/2010 | Magomet | |
| 7,838,011 B2 | 11/2010 | Abelyan | |

(Continued)

FOREIGN PATENT DOCUMENTS

| | | |
|---|---|---|
| CN | 1049666 | 3/1991 |
| CN | 1100727 | 3/1995 |

(Continued)

OTHER PUBLICATIONS

International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063.
International Search Report and Written Opinion of PCT/US2011/047498.
International Search Report and Written Opinion of PCT/US2011/047499.

(Continued)

*Primary Examiner* — Sarah Pihonak
(74) *Attorney, Agent, or Firm* — Taft Stettinius & Hollister LLP; Audrey J. Babcock

(57) ABSTRACT

Stevia extracts with selected major steviol glycosides (Reb A, stevioside, Reb D, Reb C) and minor steviol glycosides and glycosylated diterpene derivative plant molecules, derived from *Stevia rebaudiana* plant are found to improve the perception of flavor and taste perception, which includes the sweet, savory and salty perception in a wide range of food and beverage applications.

10 Claims, 7 Drawing Sheets

(56) References Cited

U.S. PATENT DOCUMENTS

Figure 2:
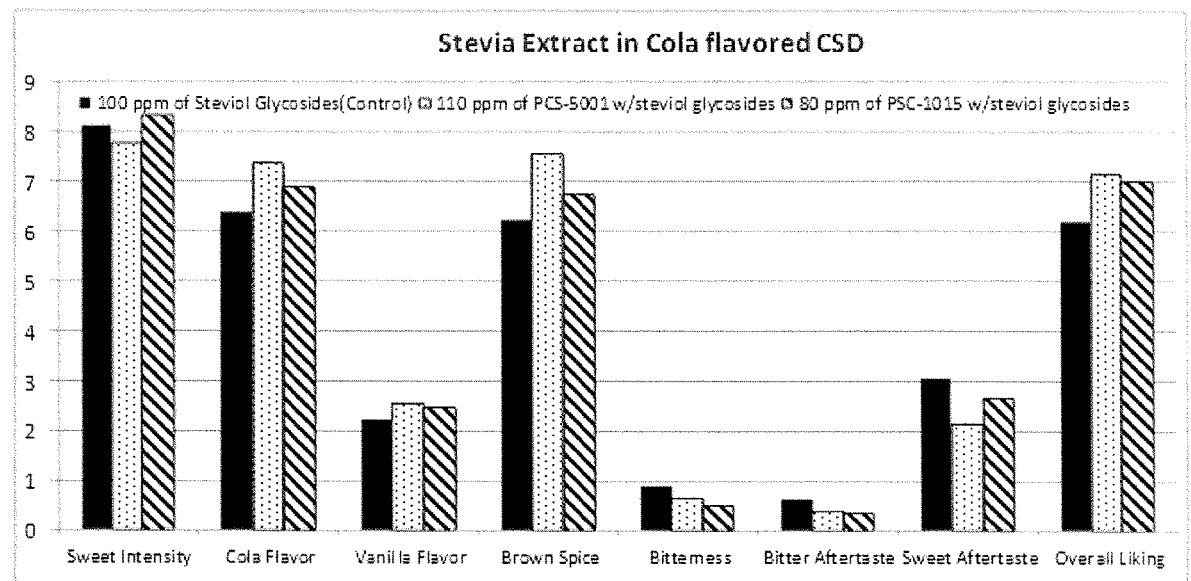

| | | |
|---|---|---|
| 7,862,845 B2 | 1/2011 | Magomet |
| 8,030,481 B2 | 10/2011 | Prakash |
| 8,257,948 B1 | 9/2012 | Markosyan |
| 8,318,459 B2 | 11/2012 | Markosyan |
| 8,647,844 B2 | 2/2014 | Markosyan |
| 8,669,077 B2 | 3/2014 | Markosyan |
| 8,735,101 B2 | 5/2014 | Markosyan |
| 8,911,971 B2 | 12/2014 | Markosyan |
| 8,993,269 B2 | 3/2015 | Markosyan |
| 9,055,761 B2 | 6/2015 | Markosyan |
| 2002/1322320 | 9/2002 | Wang |
| 2002/0187232 A1 | 12/2002 | Lee |
| 2002/0197371 A1 | 12/2002 | Lee |
| 2003/0161876 A1 | 8/2003 | Hanson |
| 2003/0232118 A1 | 12/2003 | Lerchenfeld |
| 2003/0236399 A1 | 12/2003 | Zheng |
| 2006/0083838 A1 | 4/2006 | Jackson |
| 2006/0121158 A1* | 6/2006 | Ferruzzi ............... A23C 9/152 426/72 |
| 2006/0134292 A1 | 6/2006 | Abelyan |
| 2006/0142555 A1 | 6/2006 | Jonnala |
| 2007/0082102 A1 | 4/2007 | Magomet |
| 2007/0082103 A1 | 4/2007 | Magomet |
| 2007/0082106 A1 | 4/2007 | Lee |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash |
| 2008/0064063 A1 | 3/2008 | Brandle |
| 2008/0102497 A1 | 5/2008 | Wong |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi |
| 2008/0226770 A1 | 9/2008 | Lee |
| 2008/0226794 A1* | 9/2008 | Bell ............... A23C 11/103 426/590 |
| 2008/0226797 A1 | 9/2008 | Lee |
| 2008/0292764 A1 | 11/2008 | Prakash |
| 2008/0292765 A1 | 11/2008 | Prakash |
| 2008/0292775 A1 | 11/2008 | Prakash |
| 2008/0300402 A1 | 12/2008 | Yang |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris |
| 2009/0104330 A1 | 4/2009 | Zasypkin |
| 2009/0142817 A1 | 6/2009 | Norman |
| 2009/0162499 A1 | 6/2009 | McArdle |
| 2009/0226590 A1 | 9/2009 | Fouache |
| 2010/0055752 A1 | 3/2010 | Kumar |
| 2010/0056472 A1 | 3/2010 | Duan |
| 2010/0099857 A1 | 4/2010 | Evans |
| 2010/0011215 A1 | 5/2010 | Abelyan |
| 2010/0057024 A1 | 5/2010 | Cavallini |
| 2010/0120710 A1 | 5/2010 | Watanabe |
| 2010/0013756 A1 | 6/2010 | Prakash et al. |
| 2010/0137569 A1 | 6/2010 | Prakash |
| 2010/0018986 A1 | 7/2010 | Abelyan et al. |
| 2010/0189861 A1 | 7/2010 | Abelyan |
| 2010/0227034 A1 | 9/2010 | Purkayastha |
| 2010/0255171 A1 | 10/2010 | Purkayastha |
| 2010/0278993 A1 | 11/2010 | Prakash |
| 2010/0316782 A1 | 12/2010 | Shi |
| 2011/0030457 A1 | 2/2011 | Valery |
| 2011/0033525 A1 | 2/2011 | Lui |
| 2011/0092684 A1 | 4/2011 | Abelyan |
| 2011/0104353 A1 | 5/2011 | Lee |
| 2011/0111115 A1 | 5/2011 | Shi |
| 2011/0124587 A1 | 5/2011 | Jackson |
| 2011/0160311 A1* | 6/2011 | Prakash ............... A23L 2/60 514/777 |
| 2011/0163011 A1 | 6/2011 | Prakash |
| 2011/0183056 A1* | 7/2011 | Morita ............... C07H 15/256 426/442 |
| 2011/0189360 A1 | 8/2011 | Yoo |
| 2011/0195169 A1 | 8/2011 | Markosyan |
| 2011/0224168 A1 | 9/2011 | Szente |
| 2012/0157553 A1 | 6/2012 | Dewis |
| 2012/0164678 A1 | 6/2012 | Stephanopoulos |
| 2012/0214751 A1 | 8/2012 | Markosyan |
| 2012/0214752 A1 | 8/2012 | Markosyan |
| 2012/0269954 A1* | 10/2012 | Bridges ............... A23L 2/60 426/658 |
| 2013/0030060 A1 | 1/2013 | Markosyan |
| 2013/0347140 A1 | 12/2013 | Wang |
| 2014/0271996 A1 | 9/2014 | Prakash |
| 2014/0357588 A1 | 12/2014 | Markosyan |
| 2015/0031868 A1 | 1/2015 | Lehmann |
| 2015/0157045 A1 | 6/2015 | Markosyan |

FOREIGN PATENT DOCUMENTS

| | | |
|---|---|---|
| CN | 1112565 | 11/1995 |
| CN | 1192447 | 9/1998 |
| CN | 1238341 | 5/2002 |
| CN | 1349997 | 5/2002 |
| CN | 101200480 | 6/2008 |
| CN | 101591365 | 12/2009 |
| CN | 101628924 | 1/2010 |
| EP | 0957178 | 4/1999 |
| EP | 2433505 | 3/2012 |
| EP | 2510800 | 10/2012 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |

(56) References Cited

FOREIGN PATENT DOCUMENTS

| | | |
|---|---|---|
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 59183670 | 10/1984 |
| JP | 60188035 A | 9/1985 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2000270804 | 10/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | WO2005089483 | 9/2005 |
| WO | WO2006072878 | 7/2006 |
| WO | WO2006072879 | 7/2006 |
| WO | WO2007061795 | 5/2007 |
| WO | WO2007116823 | 5/2007 |
| WO | WO2008091547 | 7/2008 |
| WO | WO2008112966 | 9/2008 |
| WO | WO2009071277 | 6/2009 |
| WO | WO2009108680 | 9/2009 |
| WO | WO2009140394 | 11/2009 |
| WO | WO2010038911 | 4/2010 |
| WO | WO2010118218 | 10/2010 |
| WO | WO2010146463 | 12/2010 |
| WO | WO2011046423 | 4/2011 |
| WO | WO2011059954 | 5/2011 |
| WO | WO2011083056 | 7/2011 |
| WO | WO2011097359 | 8/2011 |
| WO | WO2011112892 | 9/2011 |
| WO | WO2011153378 | 12/2011 |
| WO | WO2012006728 | 1/2012 |
| WO | WO2012082493 | 6/2012 |
| WO | WO2012082677 | 6/2012 |
| WO | WO2012088593 | 7/2012 |
| WO | WO2012102769 | 8/2012 |
| WO | WO2012112180 | 8/2012 |
| WO | WO2012125991 | 9/2012 |
| WO | WO2012129451 | 9/2012 |
| WO | WO2012166163 | 12/2012 |
| WO | WO2012166164 | 12/2012 |
| WO | WO2012177727 | 12/2012 |
| WO | WO2013022989 | 2/2013 |
| WO | WO2014122328 | 2/2013 |
| WO | WO2013110673 | 8/2013 |
| WO | WO2013176738 | 11/2013 |
| WO | WO2014122227 | 8/2014 |
| WO | WO2014146089 | 9/2014 |
| WO | WO2014146135 | 9/2014 |
| WO | WO2014193888 | 12/2014 |

OTHER PUBLICATIONS

International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
International Search Report and Written Opinion of PCT/US2015/047234.
Supplementary European Search Report dated Nov. 16, 2015.
Gorden et al. ("Supersaturation" Access Science McGraw Hill 2008, p. 1, http://www.accessscience.com/content/supersaturation/670000).
Huang, X Y, et al. "Preparative isolation and purification of steviol glycosides from Stevia rebaudiana Bertoni usina high-speed countercurrent chromatogoraphy".
Separation and Purification Technology Elsevier Science, Netherlands, vol. 71, No. 2, 2010, p. 220-224.
Ohtani et al. "Chapter 7. Methods to improve the taste of the sweet principles of Stevia rebaudiana." The Genus Stevia, edited by A. Douglas Kinghorn, CRC Press 2001, Taylor and Francis, London and New York, pp. 138-159.
Prakash et al., "Development of rebiana, a natural, non-caloric sweetener," Jul. 1, 2008, Food and Chemical Toxicology, vol. 46, Is. 7, Sup. 1, p. S75-S82.
Sweet Green Fields, LLC "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the Web on May 8, 2012) entire document esp. p. 22, Table 1.
Wallin, "Steviol glycosides," 2004, XP002740430 ftp://ftp.fao.org/es/esn/jecfa/cta/CTA63_Steviol.pdf, pp. 1, 4, 5. Retrieved 2015.
International Search Report and Written Opinion of PCT/US2014/041548.
a-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999, 277-282.
Chen, et al., "Selectivity of polymer adsorbent in adsorptive separations of stevia diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the Stevia plant", Chemistry in Britain, Oct. 1986, 915-916, 918.
Chatsudthipong, et al. Stevioside and related compounds: Therapeutic benefits beyond sweetness, pp. 41-45 Pharmacology & Therapeutics 121 (2009).
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.

(56) References Cited

OTHER PUBLICATIONS

Fao/Who "Combined Compendium of Food Additive Specifications" Fao Jecfa Monographs 1, vol. 4, 2006, Food and Agricultural Organization of the United Nations, Rome.
Fuh, "Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.
International Search Report and Written Opinion of PCT/US2010/055960 2010.
International Search Report and Written Opinion of PCT/US2011/028028 2011.
International Search Report and Written Opinion of PCT/US2011/033734 2011.
International Search Report and Written Opinion of PCT/US2011/033737 2011.
International Search Report and Written Opinion of PCT/US2011/033912 2011.
International Search Report and Written Opinion of PCT/US2011/035173 2011.
International Search Report and Written Opinion of PCT/US2011/036063 2011.
International Search Report and Written Opinion of PCT/US2011/047498 2011.
International Search Report and Written Opinion of PCT/US2011/047499 2011.
International Search Report and Written Opinion of PCT/US2011/064343 2011.
International Search Report and Written Opinion of PCT/US2012/024585 2012.
International Search Report and Written Opinion of PCT/US2012/024722 2012.
International Search Report and Written Opinion of PCT/US2012/030210 2012.
International Search Report and Written Opinion of PCT/US2012/043294 2012.
International Search Report and Written Opinion of PCT/US2012/051163 2012.
International Search Report and Written Opinion of PCT/US2012/052659 2012.
International Search Report and Written Opinion of PCT/US2012/052665 2013.
International Search Report and Written Opinion of PCT/US2013/030439 2015.
International Search Report and Written Opinion of PCT/US2015/047234 2015.
Supplementary European Search Report Nov. 16, 2015.
Database WPI, Week 198448, Thomas Scientific, London, GB, AN 1984-297215 XP002380834.
Gorden et al. ("Supersaturation" Access Science McGraw Hill 2008, p. 1, http://www.accessscience.corn/content/supersaturation/670000).
Hartel, Richard "Crystallization in Foods" Handbook of Industrial Crystallization Elsevier 2002, pp. 287 and 293-296.
"Recrystallization Technique: Proper purification of crystalline solids". Available online as of Dec. 4, 2009 from www.erowid.org. pp. 1-3.
Huang, X Y, et al. "Preparative isolation and purification of steviol glycosides from Stevia rebaudiana Bertoni using high-speed countercurrent chromatogoraphy" Separation and Purification Technology Elsevier Science, Netherlands, vol. 71, No. 2, 2010, pp. 220-224.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", Stevia: The genus Stevia, Taylor & Francis, 2002, 68-85.
Kinghorn, "Overview", Stevia: The genus Stevia, Taylor & Francis, 2002, 1-17.
Kitahata, S. et al., "Production of Rubusoside Derivatives by Transgalactosylation of Various b-Galactosidases" Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al.,"Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.
Moraes, et al., "Clarification of Stevia rebaudiana (Bert.) Bertoni extract adsorption in modified zeolites", Acta Scientiarum, vol. 23, No. 6 2001, 1375-1380.
News Bites, GLG announces high purity REB M GRAS notification with FDA. Consumer Durables & Apparel Melbourne. Apr. 15, 2014. pp. 1-2. especially, p. 1, para 5; p. 2, para 1.
Ohio "14.0 Spray Drying and Spray Dryers", pp. 1-10, http://class.fst.ohio-state-edu/Dairy_Tech/14Spraydrying.htm Nov. 2, 2009 as obtained by internetarchive.org.
Ohta et al., "Characterization of Novel Steviol Glycosides from Leaves of Stevia rebaudiana Morita," J. Appl. Glycosi., vol. 57, 199-209, 2010.
Ohtani et al. "Chapter 7. Methods to improve the taste of the sweet principles of Stevia rebaudiana." the Genus Stevia, edited by A. Douglas Kinghom, CRC Press 2001, Taylor and Francis, London and New York, pp. 138-159.
Philips, K.C. "Stevia: steps in developing a new sweetener", in T.H. Grenby, Editor, Developments in Sweeteners-3, Elsevier 1987, 1-43.
Pol, et al., "Comparison of two different solvents employed for pressurised fluid extraction of stevioside from Stevia rebaudiana: methanol versus water", Anal Bioanal Chem vol. 388 2007, 1847-1857.
Pol, et al., "Characterisation of Stevia Rebaudiana by comprehensive two-dimensional liquid chromatography time-of-flight mass spectrometry," Journal of Chromatography A, 1150 (2007) 85-92.
Prakash et al., "Development of rebiana, a natural, non-caloric sweetener," Jul. 1, 2008, Food and Chemical Toxicology, vol. 46, Is. 7, Sup. 1, pp. S75-S82.
Prakash et al. "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita," Biomolecules, vol. 4, 2014, 374-389, p. 385 para 5.
Prakash et al., "Development of Next Generation Stevia Sweetener: Rebaudioside M" Foods 2014, 3, 162-175, ISSN 2304-8158.
Rebaudioside A and Stevia Extract, Internet Citation, 2007 http://emperorsherbologist.com/rebaudioside_a.php.P.1-3.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.

(56) References Cited

OTHER PUBLICATIONS

Shi, et al. "Synthesis of bifuntional polymeric adsorbent and its application in purification of Stevia glycosides", Reactive & functional Polymers, vol. 50 2002, 107-116.
Shibata et al. "Glucosylation of Steviol and Steviol-Glucosides in Extracts from Stevia rebaudiana Bertoni," Plant Physiol. vol. 95, (1991) 152-156.
Starratt, et al. "Rebaudioside F, a diterpene glycoside from Stevia Rebaudiana", Phytochemistry, vol. 59 2002, 367-370.
Sweet Green Fields, LLC "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fen/gras notices/grn000282.pdf (obtained from the Web on May 8, 2012) entire document esp. p. 22, Table 1.
Tanaka, O., "Improvement of taste of natural sweeteners," Pure & Appl. Chem., vol. 69, No. 4 1997, 675-683.
Teo, et al. "Validation of green-solvent extraction combined with Chromatographic chemical fingerprint to evaluate quality of Stevia reaudiana Bertoni", J. Sep. Sci, vol. 32 2009, 613-622.
Toyo sugar, "GRAS Exemption Claim for a-Glucosylated Steviol Glycosides" Office of Food Additive Safety. Feb. 23, 2011.
United Nations' Food and Agriculture Organization/Joint Expert Committee on Food Additives (2010) Steviol Glycosides, Compendium of Food Additive Specifications, FAO JECFA Monographs 10, 17-21.
UN "Steviol Glycosides" JECFA 2008 pp. 1-4, UN "Steviol Glycosides" JECFA 2008 pp. 1-4 http://www.fao.org/ag/agn/jecfa-additives/specs/monograph5/additive-442-m5.pdf.
van der Maarel et al., "Properties and applications of starch-converting enzymes of the a-amylase family," Journal of Biotechnology, vol. 94 (220) 137-155.
Vasquez et al., Stimulation of the Gerbil's Gustatory Receptors by Some Potently Sweet Terpenoids, J. Agric. Food Chem., vol. 41, 1305-1310, 1993.
Wallin, "Steviol glycosides," 2004, XP002740430 fip://ftp.fao.org/es/esn/jecfa/cta/CTA63_Steviol.pdf, pp. 1, 4, 5. Retrieved 2015.
Yamamoto, K. et al., "Effective Production of Glycosyl-steviosides by a-1, 6 Transglucosylation of Dextrin Dextranase", Biosci. Biotech. Biochem. vol. 58, No. 9 1994, 1657-1661.
Ye, et al. "Modification of stevioside using transglucosylation activity of Bacilllus amyloliquefaciens a-amylase to reduce its bitter aftertaste," LWT-Food Science and Technology, vol. 51, Issue 1, May 2013, pp. 524-530.
Yoshikawa, et al. "Transglycosylation of Mogroside V, a Triterpene Glycoside in *Siraitia grosvenori*, by Cyclodextrin Glucanotransferase and Improvement of the Qualities of Sweetness," The Japanese Society of Applied Glycoscience, vol. 52, No. 3, 2005, pp. 247-252.
Yoda, et al. "Supercritical fluid extraction from Stevia rebaudiana Bertoni using CO2 and CO2+ water: extraction kinetics and identification of extracted components", Journal of Food Engineering, vol. 57 2003, 125-134.
Remington: The Science and Practice of Pharmacy, 21st Edition. The University of the Sciences in Philadelphia, 2006. Part 5, p. 700.
"Toxicity, Alcohols". Available online as of Jan. 29, 2010 from emedicine.medscape.com. pp. 1-4.
Zell, et al. "Investigation of Polymorphism in Aspartame and Neotame Using Solid-State NMR Spectroscopy", Tetrahedron, vol. 56, 2000, 6603-6616.
"Methanol". Available online from Sigma-Aldrich as of Jan. 4, 2016. pp. 1-2.
"Acetone". Available online from Sigma-Aldrich as of Jan. 4, 2016. pp. 1-2.
Zhang, et al. "Membrane-based separation scheme for processing sweetener from Stevia leaves", Food Research International, vol. 33 2000, 617-620.
Harman et al. "Sensory Testing for Flavorings with Modifying Properties", ift.org, No. 2013, vol. 67, No. 11, 15 pages.
Chaturvedula et al., "Two Minor Diterpene Glycosides from the Leaves of Stevia rebaudiana", Natural Product Communications, 2011, vol. 6, No. 2, pp. 175-178.
Rajbhandari et al., "The Flavonoids of Stevia Rebaudiana", Department of Pharmacognosy, Mar-Apr 1983, pp. 194-195.
Markovic et al., "Chemical composition of leaf extracts of Stevia rebaudiana Bergoni grown experimentally in Vogvodina", J. Serb. Chem. Soc. 73 (3) 283-297 (2008).
Goyal et al., "Stevia (Stevia rebaudiana) a bio-sweetener: a review", International Journal of Food Sciences and Nutrition, Feb. 2010; 61(1): pp. 1-10.
Chaturvedula et al., "Structures of the novel diterpene glycosides from Stevia rebaudiana", Carbohydrate Research 346 (2011) pp. 1057-1060.
International Search Report and Written Opinion of PCT/US2014/041548 2014.
Ohta et al., Characterization of Novel Steviol Glycosides from Leaves of Stevia rebaudiana Morita, J. Appl. Glycosci. (vol. 57), pp. 199-209 (2010), The Japanese Society of Applied Glycoscience.†

\* cited by examiner
† cited by third party

FIG. 1

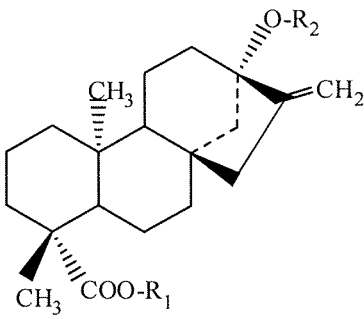

| Compound name | R₁ (C-19) | R₂ (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>    |<br>β-Glc(3→1) |
| 7. Rebaudioside B | H | β-Glc-β-Glc(2→1)<br>    |<br>β-Glc(3→1) |
| 8. Rebaudioside C (Dulcoside B) | β-Glc | β-Glc-α-Rha(2→1)<br>    |<br>β-Glc(3→1) |
| 9. Rebaudioside D | β-Glc-β-Glc(2→1) | β-Glc-β-Glc(2→1)<br>    |<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>    |<br>β-Glc(3→1) |
| 12. Dulcoside A | β-Glc | β-Glc-α-Rha(2→1) |

STEVIA EXTRACT CONTAINING SELECTED STEVIOL GLYCOSIDES AS FLAVOR, SALTY AND SWEETNESS PROFILE MODIFIER

This application is a continuation-in-part application of and claims the benefit of priority to U.S. patent application Ser. No. 61/832,451, filed Jun. 7, 2013 and Ser. No. 61/942,331, filed on Feb. 20, 2014.

FIELD OF THE INVENTION

The invention relates to the use of stevia extracts as flavor modifiers that contain mixtures of steviol glycosides extracted from *Stevia rebaudiana* plant. This invention also relates to the application of the above-said stevia extracts as sweetness profile modifier, not a sweetener, with other natural and artificial sweeteners. This invention also relates to the production and use of the above-mentioned stevia extracts that can be used as flavor and sweetness profile modifier when used in food, beverage, and pharmaceutical products.

DESCRIPTION OF THE RELATED ART

High intensity sweeteners possess sweetness level many times exceeding that of sucrose. They are essentially non-caloric and used widely in manufacturing of diet and reduced calorie food. Although natural caloric sweetener such as sucrose, fructose, and glucose provide the most desirable taste to consumers, they are caloric. High intensity sweeteners do not affect the blood glucose level and provide little or no nutritive value.

However, high intensity sweeteners that generally are used as substitutes for sucrose possess taste characteristics different than that of sugar, such as sweet taste with different temporal profile, maximal response, flavor profile, mouthfeel, and/or adaptation behavior than that of sugar. For example, the sweet taste of some high-potency sweeteners is slower in onset and longer in duration than that of sugar and thus changes the taste balance of a food composition. Because of these differences, usage of high-potency sweetener in replacing such a bulk sweetener as sugar in a food or beverage causes imbalance in temporal and/or flavor profile. If the taste profile of high-potency sweeteners could be modified to impart desired taste characteristics, it can provide low calorie beverages and food products with taste characteristics more desirable for consumers. To attain the sugar-like temporal and/or flavor profile, several ingredients have been suggested in different publications.

Non-limiting examples of synthetic sweeteners include sucralose, potassium acesulfame, aspartame, alitame, saccharin, neohesperidin dihydrochalcone synthetic derivatives, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]L-phenylalanine 1-methyl ester, salts thereof, and the like.

Non-limiting examples of natural high intensity sweeteners include Stevioside, Rebaudioside A, Rebaudioside B, Rebaudioside C, Rebaudioside E, Rebaudioside F, Steviolbioside, Dulcoside A, Rubusoside, mogrosides, brazzein, neohesperidin dihydrochalcone (NHDC), glycyrrhizic acid and its salts, thaumatin, perillartine, pernandulcin, mukuroziosides, baiyunoside, phlomisoside-I, dimethyl-hexahydro-fluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside and others.

High intensity sweeteners can be derived from the modification of natural high intensity sweeteners, for example, by fermentation, enzymatic treatment, or derivatization.

A growing number of consumers perceive the ability to control their health by enhancing their current health and/or hedging against future diseases. This creates a demand for food products with enhanced characteristics and associated health benefits, specifically a food and consumer market trend towards "whole health solutions" lifestyle. The term "natural" is highly emotive in the world of sweeteners and has been identified as one of key trust, along with "whole grains", "heart-healthy" and "low-sodium". 'Natural' term is closely related to 'healthier'.

*Stevia rebaudiana* is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local beverages, foods and medicines.

At present there are more than 230 *Stevia* species with significant sweetening properties. The plant has been successfully grown under a wide range of conditions from its native subtropics to the cold northern latitudes.

Steviol glycosides have zero calories and can be used wherever sugar is used. They are ideal for diabetic and low calorie diets. In addition, the sweet steviol glycosides possess functional and sensory properties superior to those of many high potency sweeteners.

The extract of *Stevia rebaudiana* plant contains a mixture of different sweet diterpene glycosides, which have a single base—steviol and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6%), Rebaudioside A (3.8%) and Stevioside (9.1%). Other glycosides identified in Stevia extract include Rebaudioside B, C, D, E, and F, Steviolbioside and Rubusoside (FIG. 1).

The chemical structures of the diterpene glycosides of *Stevia rebaudiana* are presented in FIG. 1. The physical and sensory properties are well studied only for Stevioside and Rebaudioside A. The sweetness potency of Stevioside is around 210 times higher than sucrose, Rebaudioside A around 300 times, and Rebaudioside C and Dulcoside A around 30 times. The Stevia extract containing Rebaudioside A and Stevioside as major components showed sweetness potency around 250 times. Rebaudioside A and Rebaudioside D are considered to have most favorable sensory attributes of all major Steviol Glycosides (TABLE 1).

TABLE 1

| Name | Formula | $T_{Melt}$, °C | Mol. Weight | Solubility in water, % | Relative sweetness | Quality of taste |
|---|---|---|---|---|---|---|
| Steviol | $C_{20}H_{30}O_3$ | 212-213 | 318.45 | ND | ND | Very bitter |
| Steviolmonoside | $C_{26}H_{40}O_8$ | ND | 480.58 | ND | ND | ND |
| Stevioside | $C_{38}H_{60}O_{18}$ | 196-198 | 804.88 | 0.13 | 210 | Bitter |
| Rebaudioside A | $C_{44}H_{70}O_{23}$ | 242-244 | 967.01 | 0.80 | 200-400 | Less Bitter |
| Rebaudioside B | $C_{38}H_{60}O_{18}$ | 193-195 | 804.88 | 0.10 | 150 | Bitter |
| Rebaudioside C | $C_{44}H_{70}O_{22}$ | 215-217 | 951.01 | 0.21 | 30 | Bitter |
| Rebaudioside D | $C_{50}H_{80}O_{28}$ | 248-249 | 1129.15 | 1.00 | 220 | Like sucrose |
| Rebaudioside E | $C_{44}H_{70}O_{23}$ | 205-207 | 967.01 | 1.70 | 170 | Like sucrose |
| Rebaudioside F | $C_{43}H_{68}O_{22}$ | ND | 936.99 | ND | ND | ND |
| Dulcoside A | $C_{38}H_{60}O_{17}$ | 193-195 | 788.87 | 0.58 | 30 | Very bitter |
| Steviolbioside | $C_{32}H_{50}O_{13}$ | 188-192 | 642.73 | 0.03 | 90 | Unpleasant |
| Rubusoside | $C_{32}H_{50}O_{13}$ | ND | 642.73 | ND | 110 | Very bitter |

In addition to the commercially known steviol glycosides (Table 1), several new steviol glycosides (Glycosylated diterpene) have been found in *stevia* leaf extracts (5,6,7) as shown in Table 2. Besides diterpene glycosides, a number of flavonoids, labdane diterpene, triterpenes, sterols, and volatile oils have also been reported in the extracts of *Stevia rebaudiana* [1, 2, 3, 4]

TABLE 2

| Chemical Classes | Chemical Components |
|---|---|
| Glycosylated diterpene derivatives | Rebaudioside G, Rebaudioside H, Rebaudioside I, Rebaudioside J, Rebaudioside K, Rebaudioside L Rebaudioside M, Rebaudioside N, Rebaudioside O, 13-[(2-O-(6-O-β-D-glucopyranosyl)-β-Dglucopyranosyl-β-D-glucopyranosyl)oxy] kaur-16-en-18-oic acid □-D-glucopyranosyl ester, 13-[(2-O-β-D-glucopyranosyl-3-O-β-D-fructofuranosyl-β-D-glucopyranosyl) oxy] kaur-16-en-18-oic acid β-D-glucopyranosyl ester |
| Monoterpenoids | Borneol |
| Diterpenoids | Austroinulin, 6-0-acetyl austroinulin, 6-acetyl austroinulin 7-0-acetyl austroinulin, Sterebin A, B, C, D, E, F, G, H, Jhanol |
| Triterpenoids | Amyrin beta acetate |
| Sesquiterpenes | α-bergamotene, Bisabolene, β-bourbonene, δ-cadinene, γ-cadinene |
| Essential oils | β-caryophyllene, Trans β-tarnesene, α-humulene, δ-cadiene caryophyllene oxide, Nerolidol, Linalol, α-terpineol, Terpinen-4-ol |
| Sterol derivatives | Stigmasterol, β-sitosterol, Campesterol |
| Flavonoids | Glucosyl-4'-O-apigenin, Glucosyl-7-O-luteolin, Rhamnosyl-3-O-kaempferol, Quercetin, Glucosyl-3-O-quercetin, Arabinosyl-3-O-quercetin, 5,7,3'-methoxyflavone, 3,6,4'-methoxyflavone, Centaureidin, avicularin |

All steviol glycosides provide sweetness and other taste attributes at a higher than certain threshold level of concentrations in water. Below the threshold level of concentration, the steviol glycoside components and their mixtures as found in a typical non-limiting *stevia* extract as shown below has no recognizable sweetness taste. But such stevia extract below the threshold level of significant sweetness recognition show remarkable characteristics of sweet and flavor profile modification in food and beverage applications.

This invention relates to use of the following stevia extracts (Table 3) with the varying level of different steviol glycosides and other *stevia* plant-derived glycosides, the combination of which contributes no significant sweetness but modifies flavor and sweetness profile at certain concentration in typical food and beverage applications.

TABLE 3

| | Steviol Glycosides*, % | | | | | | | | | | | | | |
|---|---|---|---|---|---|---|---|---|---|---|---|---|---|---|
| Stevia Extracts | Reb A | Stevioside | Reb D | Reb F | Reb C | Dulcoside A | Rubusoside | Reb B | Steviolbioside | Reb E | Reb N | Reb O | TSG* (%) | Other glycosides |
| PCS-5001 | 10-20 | 4-12 | 1-4 | 1-5 | 10-25 | 1-5 | 1-4 | 0.5-5 | 0.5-5 | 1-4 | 0.5-4 | 0.5-4 | 45-65 | 35-50 |
| PCS-1015 | 18-25 | 5-10 | 8-20 | 0-1 | 1-3 | 0-1 | 0-1 | 0.5-5 | 0-1 | 2-6 | 4-8 | 3-8 | 55-65 | 35-45 |

*TSG or Total Steviol Glycosides contain nine Steviol Glycosides that are recognized by Codex Alimentarius (a commission of FAO and WHO) and major regulatory authorities The present invention also relates to the stevia extracts that contain major steviol glycosides (Table 3) and other minor steviol glycosides and glycosylated diterpene derivatives (water soluble molecules). The non-limiting examples of such minor molecules are Reb E, Reb G, Reb H, Reb I, Reb K, Reb L, Reb M, Reb N, Reb O (Ohta et al, 2010).

The present invention is also directed to a method of making a specific *stevia* extract composition, including: extracting steviol glycosides and other water soluble molecules from leaves of a *Stevia rebaudiana* plant, and separating the excess steviol glycosides than the amount and type of steviol glycosides required to contribute the taste and flavor modifying characteristics of the stevia extract.

This invention combine the different natural sweeteners, especially steviol glycosides in certain proportion along with other water soluble molecules to provide enhanced sweetness and flavor profile in food and beverage application, which can be blended with other natural caloric sweeteners to impart more desirable sweetness profile. Non-limiting examples of caloric sweeteners include dextrose, fructose, sucrose, maltose, lactose, corn syrup, gluco-syrup derived from different carbohydrates, cane syrup, flavored sugar, honey, molasses, This invention combine the different natural sweeteners, especially steviol glycosides in certain proportion along with other water soluble molecules to provide enhanced sweetness and flavor profile in food and beverage application, which can be blended with other natural non-caloric sweeteners to impart more desirable sweetness profile. Non-limiting examples of natural high intensity sweeteners include steviol glycosides, brazzein, monatin and its salt, neohesperidin dihydrochalcone (NHDC), glycyrrhizic acid and its salts, thaumatin, mogrosides and lu han guo extracts, perillartine, mabinlin, pentadin, miraculin, curculin, neoculin, chlorogenic acid, cynarin, siamenoside and others.

This invention combine the different natural sweeteners, especially steviol glycosides in certain proportion along with other water soluble molecules to provide enhanced sweetness and flavor profile in food and beverage application, which can be blended with other synthetic non-caloric sweeteners to impart more desirable sweetness profile. Non-limiting examples of synthetic sweeteners include sucralose, potassium acesulfame, aspartame, alitame, advantame, saccharin, neohesperidin dihydrochalcone synthetic derivatives, cyclamate, neotame, dulcin, suosan, N—[N-[3-(3-hydroxy-4-methoxyphenyl)propyl]-L-☐-aspartyl]-L-phenyl alanine 1-methyl ester, N—[N-[3-(3-hydroxy-4-methoxyphenyl)-3-methylbutyl]-L-☐-aspartyl]-L-phenylalanine 1-methyl ester, N—[N-[3-(3-methoxy-4-hydroxyphenyl) propyl]-L-☐-aspartyl]-L-phenylalanine 1-methyl ester, salts thereof, and the like.

BRIEF SUMMARY OF THE INVENTION

The present invention is directed to a taste and flavor modifying composition. The composition includes different steviol glycosides with other water soluble molecules derived from *Stevia* leaf, such as non-limiting examples of plant glycosides, flavonoids, labdane diterpene, triterpenes, which can modify the intensity of a taste and/or a flavor in a food or beverage product.

The present invention is also directed to a food or beverage product having an intense taste and flavor profile, wherein the food or beverage product includes a taste and flavor modifying composition comprising the stevia extract of steviol glycosides and water soluble molecules derived from *stevia* plant. A wide range of food and beverage products, such as, but not limited to, carbonated soft drinks, fruit juices, dairy foods, dairy beverages, baked goods, cereal products, snack foods, and table top sweeteners, may be made in accordance with the present invention. The taste and flavor profile of a food or beverage product including a taste and flavor modifying composition, wherein the taste and flavor modifying composition comprising the stevia extract of steviol glycosides and water soluble molecules derived from *stevia* plant, may be more intense than a comparative taste and flavor profile of a comparative food or beverage product which does not include the taste and flavor modifying composition. Moreover, the mouthfeel and overall taste perception of a food or beverage product including the taste and flavor modifying composition, wherein the taste and flavor enhancing composition includes the complex mixture of steviol glycosides and water soluble molecules, may be improved in relation to a mouthfeel and overall taste perception of a comparative food or beverage product which does not include the taste and flavor enhancing composition.

The present invention is further directed to a method of increasing the taste and flavor intensity of a food or beverage product, including the step of adding a taste and flavor enhancing composition to the food or beverage product, wherein the taste and flavor modifying composition comprising the stevia extract of steviol glycosides and water soluble molecules derived from *stevia* plant. The present invention is also directed to a method of improving the organoleptic properties of a food or beverage product including a high fructose syrup, including the step of adding the taste and flavor modifying composition to the food or beverage product. For example, adding the taste and flavor modifying composition may cause the high fructose syrup, such as high fructose corn syrup, to taste more like sugar. Also, if the high fructose syrup is high fructose corn syrup 42 (HFCS 42), adding the taste and flavor enhancing composition may cause the HFCS 42 to taste more like high fructose corn syrup 55 (HFCS 55).

The present invention is further directed to a method of increasing the taste and flavor intensity of a medical food and pharma product, including the step of adding a taste and flavor modifying composition to the food or beverage product, wherein the taste and flavor modifying composition comprising the stevia extract of selected steviol glycosides and water soluble molecules derived from *stevia* plant. The present invention is also directed to a method of improving the organoleptic properties of a medical food or pharma product containing functional food ingredients like vitamins, minerals and amino acids, including the step of adding the taste and flavor modifying composition to the food or beverage product. For example, adding the taste and flavor modifying composition may cause the off-taste due to vitamins, mineral, amino acids and other non-limiting functional ingredients, to improve taste and palatability.

The present invention is also directed to a method of making a taste and flavor enhancing composition, including: extracting steviol glycosides and other water soluble molecules from leaves of a Stevia rebaudiana plant, and separating the excess steviol glycosides than the amount and type of steviol glycosides required to contribute the taste and flavor modifying characteristics of the stevia extract.

The foregoing has outlined rather broadly the features and technical advantages of the present invention in order that the detailed description of the invention that follows may be better understood. Additional features of the invention which form the subject of the claims of the invention will be described hereinafter. It should be appreciated by those skilled in the art that the specific embodiments disclosed may be readily utilized as a basis for modifying or designing other methods or structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description.

EXAMPLES

Example 1A

Detection of Concentration Threshold for Sweetness Recognition

To detect the sweetness recognition level of PCS-5001 (stevia extract), the test method outlined by Harman, et al (Food Technology, November 2013) was used with ten trained panelists that have been previously qualified for their taste acuity and trained in the use of a sweetness intensity rating scale, evaluated a series of aqueous solutions of sucrose and the stevia extract (PCS-5001 or PCS-1015) at room temperature; the sucrose solutions of 1.5% concentration and the stevia extract solutions with concentrations ranging between 100 and 120 ppm for PCS-5001 and 70-80 ppm for PCS-1015 were prepared with filter water. The objective of the test was to determine the sweetness recognition level of the stevia extract. The evaluations were done in triplicate using the same panelists so that a total of 30 values were generated for each average data point.

The samples were coded and presented in random order to panel members to taste and determine which sample was sweeter (ASTM E2164-08: Standard Method for Directional Difference Test). Panelists were asked to focus only on sweet attribute of those samples and to use warm water and salt solution in order to cleanse the palate between samples.

The results were tallied and significance was calculated by SIM 2000 (Sensory Computer System, NJ). Results are presented in Table 4. The overall sweetness of those samples was barely detectable. The 2-AFC shows that 100 ppm PCS-5001 and 70 ppm of PCS-1015 solution were the least sweet sample and were significantly less sweet then the 1.5% sugar control. The sample with 120 ppm PCS-5001 and 80 ppm PCS-1015 were the sweetest samples showing significantly higher sweetness than the 1.5% sugar control (Table 4). The recognition threshold concentration of STEVIA EXTRACT (PCS-5001) in water was determined to be 100 ppm. The recognition threshold concentration of STEVIA EXTRACT (PCS-1015) in water was determined to be 70 ppm.

TABLE 4

Sweetness perception of Stevia Extract in different concentration against 1.5% sugar solution.

| Comparison of sweetness perception of STEVIA EXTRACT in water | Sugar solution (1.5%) sweeter? | Stevia Extract solution sweeter? | P-Value | Significance |
| --- | --- | --- | --- | --- |
| PCS-5001: 100 ppm, N = 30 | 23 | 7 | 0.0052 | *** |
| PCS-5001: 110 ppm, N = 30 | 20 | 10 | 0.0987 | ** |
| PCS-5001: 120 ppm, N = 30 | 9 | 21 | 0.0457 | *** |
| PCS-1015: 70 ppm, N = 30 | 26 | 4 | 0.0001 | *** |
| PCS-1015: 80 ppm, N = 30 | 5 | 25 | 0.0003 | *** |

Example 1B

Sweetness Detection of Concentration Threshold for Sweetness Detection

The ten panel members evaluated a series of lemon-lime flavored carbonated soft drink (CSD) sweetened with sucrose and STEVIA EXTRACT at room temperature; the evaluations were done in triplicate using the same panelists so that at least 30 values were generated for each average data point. The lemon lime flavored carbonated soft drink control sample had 1.5% sucrose concentration and the test sample contained STEVIA EXTRACT (PCS-5001) with concentrations at 110 and 120 ppm or STEVIA EXTRACT (PCS-1015) with concentrations of 70 and 90 ppm. Other ingredients in the CSD samples were citric acid, lemon-lime flavor, sodium benzoate, potassium citrate and xanthan gum. The objective of the test was to determine the sweetness detection limit of STEVIA EXTRACT. Tests were conducted as outlined in Example 1A.

The samples with 120 ppm PCS-5001 (STEVIA EXTRACT) and 90 ppm PCS-1015 (STEVIA EXTRACT) showed no significant difference in sweetness than the 1.5% sugar control. The recognition threshold concentration of PCS-5001 (STEVIA EXTRACT) in a lemon-lime flavored carbonated soft drink water was determined to be 110 ppm. The recognition threshold concentration of PCS-1015 (STEVIA EXTRACT) in a lemon-lime flavored carbonated soft drink water was determined to be 70 ppm. Results are shown in table 5.

TABLE 5

Sweetness perception of STEVIA EXTRACT in different concentrations against 1.5% sugar solution in a typical carbonated soft drink (CSD)

| Sweetness perception of STEVIA EXTRACT in CSD | CSD sample with Sugar sweeter? | CSD sample with Stevia Sweeter? | P-Value | Significance |
| --- | --- | --- | --- | --- |
| PCS-5001: 110 ppm, N = 30 | 23 | 7 | 0.0052 | *** |

TABLE 5-continued

Sweetness perception of STEVIA EXTRACT in different concentrations against 1.5% sugar solution in a typical carbonated soft drink (CSD)

| Sweetness perception of STEVIA EXTRACT in CSD | CSD sample with Sugar sweeter? | CSD sample with Stevia Sweeter? | P-Value | Significance |
|---|---|---|---|---|
| PCS-5001: 120 ppm, N = 36 | 20 | 16 | 0.677 | NS |
| PCS-1015: 70 ppm, N = 30 | 21 | 9 | 0.0428 | *** |
| PCS-1015: 90 ppm, N = 30 | 12 | 18 | 0.3616 | NS |

TABLE 6-continued

Cola flavored Soft drink for sensory evaluation

| COLA BEVERAGE FORMULA | Control: 30% Sugar Reduction | Test: 30% Sugar Reduction with PCS-5001 | Test: 30% Sugar Reduction with PCS-1015 |
|---|---|---|---|
| Cola Flavor - Flavor Systems | 0.375 | 0.375 | 0.375 |
| Phosphoric Acid 85% | 0.0333 | 0.0333 | 0.0333 |
| Caffeine | 0.0100 | 0.0100 | 0.0100 |
| Stevia glycoside | 0.0100 | 0.0100 | 0.0100 |
| PCS-5001 | | 0.0110 | |
| PCS-1015 | | | 0.0080 |
| Total | 100 | 100 | 100 |

TABLE 7

Sensory evaluation of Cola flavored carbonated soft drink

| | |
|---|---|
| Nature of Participants: | Company employees |
| Number of Sessions | 1 |
| Number of Participants: | 30 |
| Test Design: | Balanced, randomized within pair. Blind |
| Sensory Test Method: | Intensity and acceptance ratings |
| Environmental Condition | Standard booth lighting |
| Attributes and Scales: | Overall Acceptance on a 10-pt hedonic scale where 10 = Extremely Like and 0 = Extremely Dislike Overall Liking, Sweetness, Vanilla flavor, Brown note, and Sweet Aftertaste. 10-pt continuous intensity scale where 0 = Imperceptible and 10 = Extremely Pronounced |
| Statistical Analysis: | ANOVA (by Block) with Post Hoc Duncan's Test |
| Sample Size | ~1.5 oz. in a clear capped plastic cup |
| Serving Temperature | Refrigerated temperature (~45° F.) |
| Serving/Panelists Instruction: | Samples served simultaneously. Panelists instructed to read ingredient statement, evaluate each sample. |

Example 2

Effect of Stevia Extract on Flavor Modification in a Typical Carbonated Soft Drink Application A cola flavored carbonated soft drink was developed to evaluate the effect of PCS-5001 and PCS-1015 (stevia extract) on the sweetness and flavor profile of the beverage that was sweetened with sugar and stevia sweetener to achieve 30% sugar reduction (Table 6). The samples with and without PCS-5001 or PCS-1015 were evaluated by thirty consumer panel members, who assigned relative values to each sample for overall Liking, sweetness, vanilla flavor, brown note, and aftertaste on a 10-pt continuous intensity scale as outlined in Table 7.

TABLE 6

Cola flavored Soft drink for sensory evaluation

| COLA BEVERAGE FORMULA | Control: 30% Sugar Reduction | Test: 30% Sugar Reduction with PCS-5001 | Test: 30% Sugar Reduction with PCS-1015 |
|---|---|---|---|
| Water | 91.68 | 91.67 | 91.67 |
| Sugar | 7.89 | 7.89 | 7.89 |

FIG. 2 shows the modification of flavor and sweetness profiles caused by the addition of stevia extract (PCS-5001). The results indicated the sample containing stevia extract PCS-5001 and the sample containing PCS-1015 had significantly higher cola flavor, vanilla flavor, brown spice notes and overall liking compared to the control samples (at 95% confidence). The sample containing PCS-5001 had directionally lower bitterness, and bitter aftertaste intensity compared to the control samples (at 90% and 95% confidence respectively). The sample containing PCS-1015 had directionally lower bitterness, and sweet aftertaste intensity compared to the control samples (at 80% confidence). In addition, the sample with stevia extract (PCS-1015) had significantly lower bitter aftertaste compared to the control sample (at 95% confidence).

Example 3

Peach Flavored Tea Beverage for Sensory Evaluation

A peach flavored black tea drink was developed to evaluate the effect of STEVIA EXTRACT on the sweetness and flavor profile of the beverage that was sweetened with sugar and stevia sweetener to achieve 30% sugar reduction (Table 8). The samples with and without STEVIA EXTRACT were evaluated as outlined in EXAMPLE 2 by thirty consumer panel members, who assigned relative values to sweetness, bitterness, peach flavor, tea flavor, acid intensity, astringency, and aftertaste on 10-pt continuous intensity scale where 0=Imperceptible and 10=extremely pronounced.

TABLE 8

Peach Flavored Tea Beverage samples for sensory evaluation

|  | Reduced Sugar Tea | Reduce Sugar Tea with PCS-5001 | Reduce Sugar Tea with PCS-1015 |
|---|---|---|---|
| Water | 95.71 | 95.70 | 95.71 |
| Sucrose | 3.850 | 3.850 | 3.850 |
| Black Tea Powder | 0.275 | 0.275 | 0.275 |
| Citric Acid | 0.0880 | 0.0880 | 0.0880 |
| Peach Flavor | 0.0330 | 0.0330 | 0.0330 |
| Sodium Citrate | 0.0150 | 0.0150 | 0.0150 |
| Potassium Sorbate | 0.0150 | 0.0150 | 0.0150 |
| *Stevia* Glycoside | 0.0140 | 0.0140 | 0.0140 |
| *Stevia* Extract PCS-5001 |  | 0.0120 |  |
| *Stevia* Extract PCS-1015 |  |  | 0.0080 |
| Xanthan Gum - TIC | 0.0013 | 0.0013 | 0.0013 |

Figure 3:
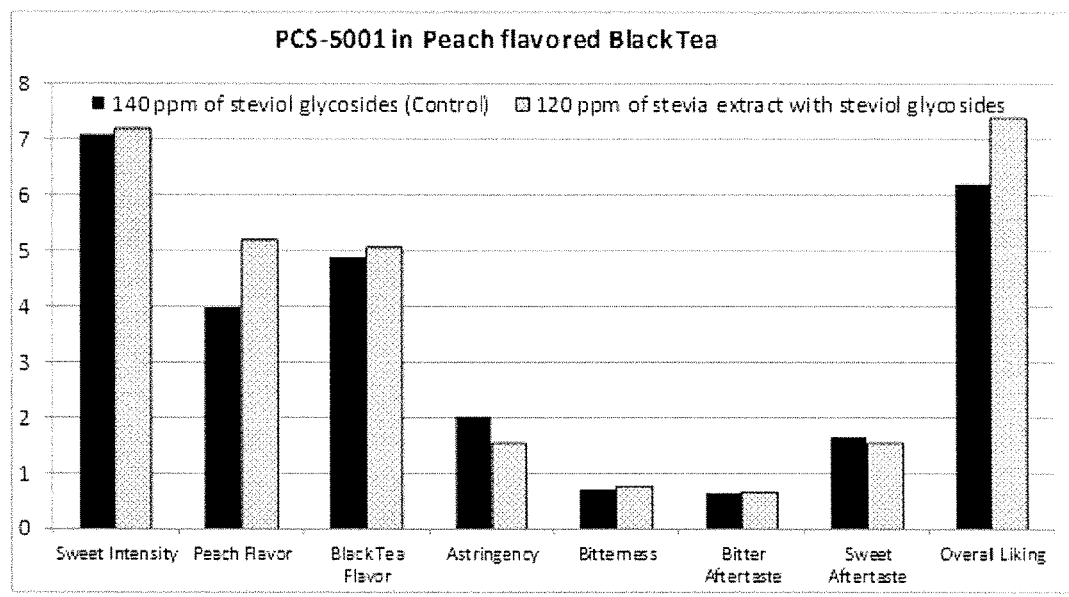
Figure 4:
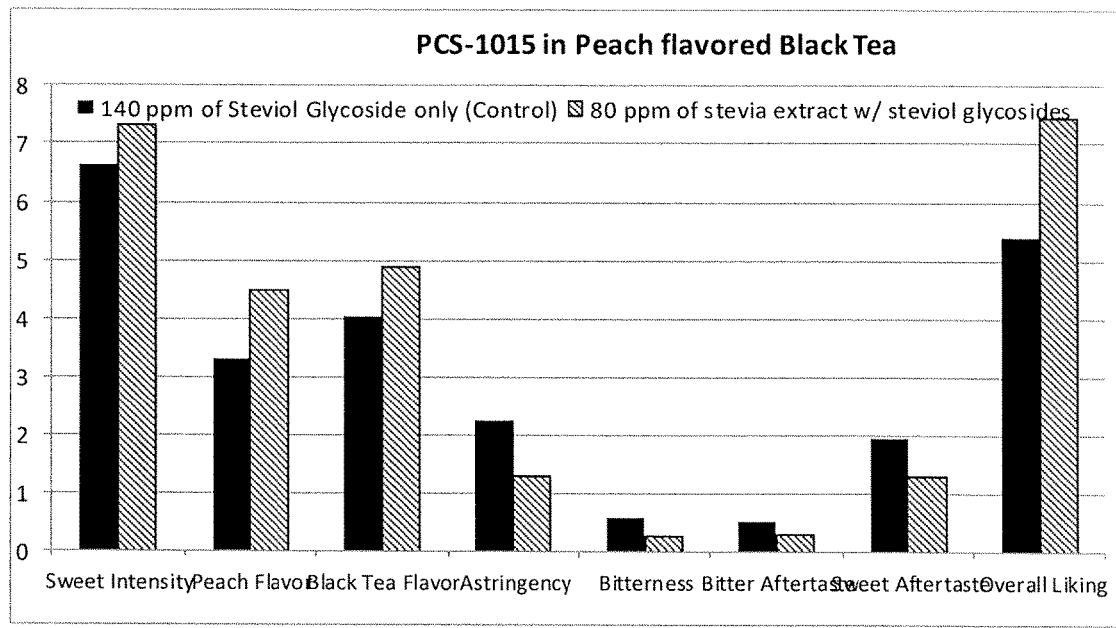

FIG. 3 shows the modification of flavor and sweetness profiles contributed by the addition of STEVIA EXTRACT (PCS-5001) in peach flavored ice tea beverage. The results indicated that the test sample containing PCS-5001 had significantly higher peach flavor, and overall liking (at 95%, confidence). The sample containing PCS-5001 had significantly lower astringency than the control sample (at 95% confidence). The results shown in FIG. 4 indicated that the test sample containing PCS-1015 had significantly higher peach flavor, black tea flavor, and overall liking (at 95%, confidence). The sample PCS-1015 also had significantly lower astringency, sweet intensity, bitter intensity, and bitter aftertaste than the Control sample (at 95% confidence). In addition, the PCS-1015 sample had lower sweet aftertaste intensity than the Control sample at 90% confidence).

Example 4

Effect of Stevia Extract on Flavor Modification of Savory Applications

A seasoning blend was developed to determine the flavor modification effect of stevia extract in a seasoning blend on reduced sugar roasted peanut samples. Thirty consumer panel members evaluated two samples of the peanuts for overall acceptance and attribute intensities (overall flavor, saltiness, sweetness, smoke flavor, spice/heat intensity, peanut flavor, chili powder flavor, bitterness and lingering sweet aftertaste intensity). The two samples (Table 9) included: 1) 50% sugar reduced control sample containing *stevia* glycosides, and 2) 50% reduced sugar test sample containing steviol glycoside and stevia extract, PCS-5001 or PCS-1015.

Figure 5:
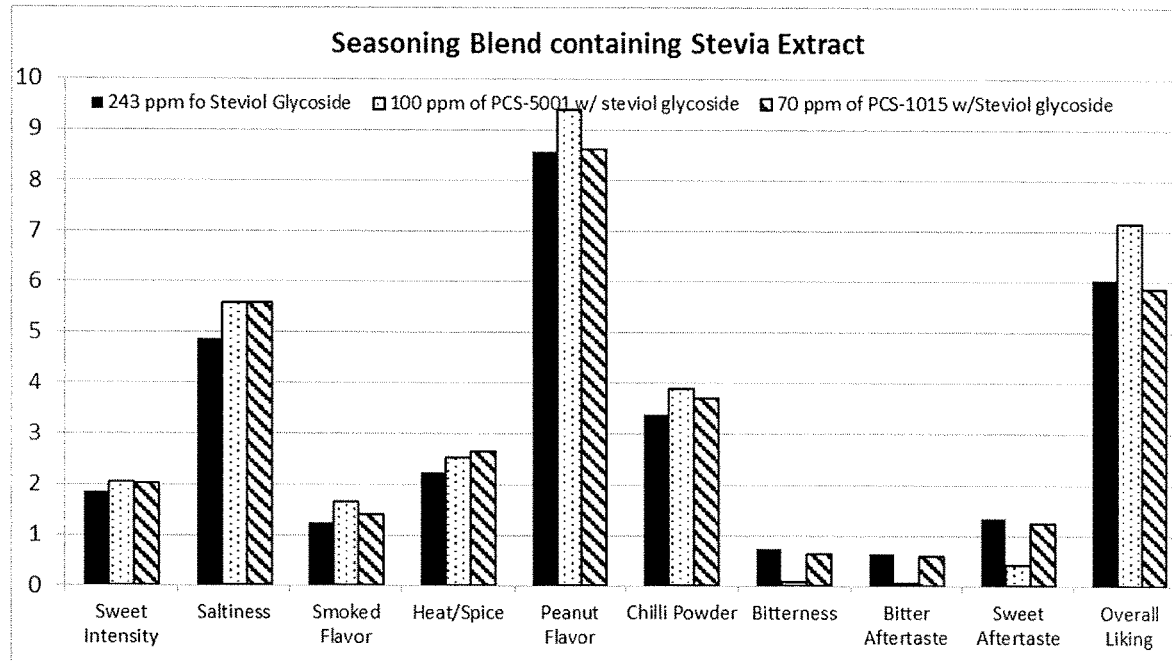

The objective of the test was to determine if the addition of stevia extract affects the flavor profile of a savory snack food. The results indicated that the addition of PCS-5001 at 110 ppm and PCS-1015 at 70 ppm provided flavor modification (FIG. 5). The test samples containing 110 ppm PCS-5001 had significantly higher salt intensity, smoke flavor, and bitter intensity compared to the control (95% confidence). The test sample also had lower sweet intensity than the control (95% confidence). In addition, the test sample containing stevia extract had directionally higher spice and chili notes (90% confidence). The test sample containing PCS-1015 had significantly higher salt intensity than the control sample (at 95% confidence). The test sample showed an increase in heat/spice intensity, and chili flavor compared to the control.

TABLE 9

Effect of *STEVIA* EXTRACT on snack and seasoning applications

|  | Steviol Glycoside | Steviol Glycoside + *Stevia* Extract | Steviol Glycoside + *Stevia* Extract |
|---|---|---|---|
| Unsalted Peanuts | 86.8 | 86.8 | 86.8 |
| Vegetable oil | 2.93 | 2.93 | 2.93 |
| Sugar | 5.88 | 5.88 | 5.88 |
| Salt | 2.93 | 2.93 | 2.93 |
| Chilli powder | 0.174 | 0.174 | 0.174 |
| Cumin powder | 0.286 | 0.286 | 0.286 |
| Garlic powder | 0.156 | 0.156 | 0.156 |
| Cayenne pepper | 0.156 | 0.156 | 0.156 |
| Smoke liquid | 0.729 | 0.729 | 0.729 |
| Steviol Glycoside | 0.0243 | 0.0243 | 0.0243 |
| PCS-5001 |  | 0.0110 |  |
| PCS-1015 |  |  | 0.0070 |
| Total wt. (g) | 100 | 100 | 100 |

TABLE 10

Sensory evaluation of snack and seasoning applications

| Nature of Participants: | Company employees |
|---|---|
| Number of Sessions | 1 |
| Number of Participants: | 30 |
| Test Design: | Balanced, randomized within pair. Blind |
| Sensory Test Method: | Intensity and acceptance ratings |
| Environmental Condition | Standard booth lighting |
| Attributes and Scales: | Overall Acceptance on a 9-pt hedonic scale where 9 = Like Extremely, 5 = Neither Like Nor Dislike, and 1 = Dislike Extremely Overall Flavor, Saltiness, Sweetness, Smoke Intensity, Heat/spice intensity, peanut flavor, chili powder and Aftertaste Intensity (sweet and bitter) on a 10-pt continuous intensity scale where 0 = Imperceptible and 10 = Extremely Pronounced |
| Open Ended General Comments | |
| Statistical Analysis: | ANOVA (by Block) with Post Hoc Duncan's Test |
| Sample Size | ~1.5 oz. in a clear capped plastic cup |
| Serving Temperature | Room temperature (~70° F.) |
| Serving/Panelists | Samples served simultaneously. |
| Instruction: | Panelists evaluate each sample once. |

Example 5

Flavor Modification of Sauce and Vegetable Preparation

A tomato ketchup preparation was developed to determine the flavor modification effect of stevia extract (PCS-1015). A panel of thirty company employees evaluated the overall acceptance and attribute intensities (tomato, onion, vinegar, sweet, saltiness, bitterness and aftertaste) of each sample. The sensory evaluation methodology outlined in Example 4 was adopted for the sauce samples as presented in Table 11.

TABLE 11

Effect of PCS-1015 (stevia extract) on tomato ketchup

|  | Steviol Glycoside | Steviol Glycoside w/Stevia Extract |
| --- | --- | --- |
| Tomato Juice (Sieved) | 52.4863 | 52.4793 |
| Tomato Puree | 24.6236 | 24.6236 |
| White Distilled Vinegar | 11.3454 | 11.3454 |
| Water | 1.5845 | 1.5845 |
| Sucrose | 2.6511 | 2.6511 |
| Tomato Paste | 5.8311 | 5.8311 |
| Onion Powder | 0.8649 | 0.8649 |
| Salt | 0.5811 | 0.5811 |
| Steviol glycoside | 0.032 | 0.032 |
| Stevia Extract (PCS 1015) |  | 0.007 |
| Total | 100 | 100 |

Figure 6:
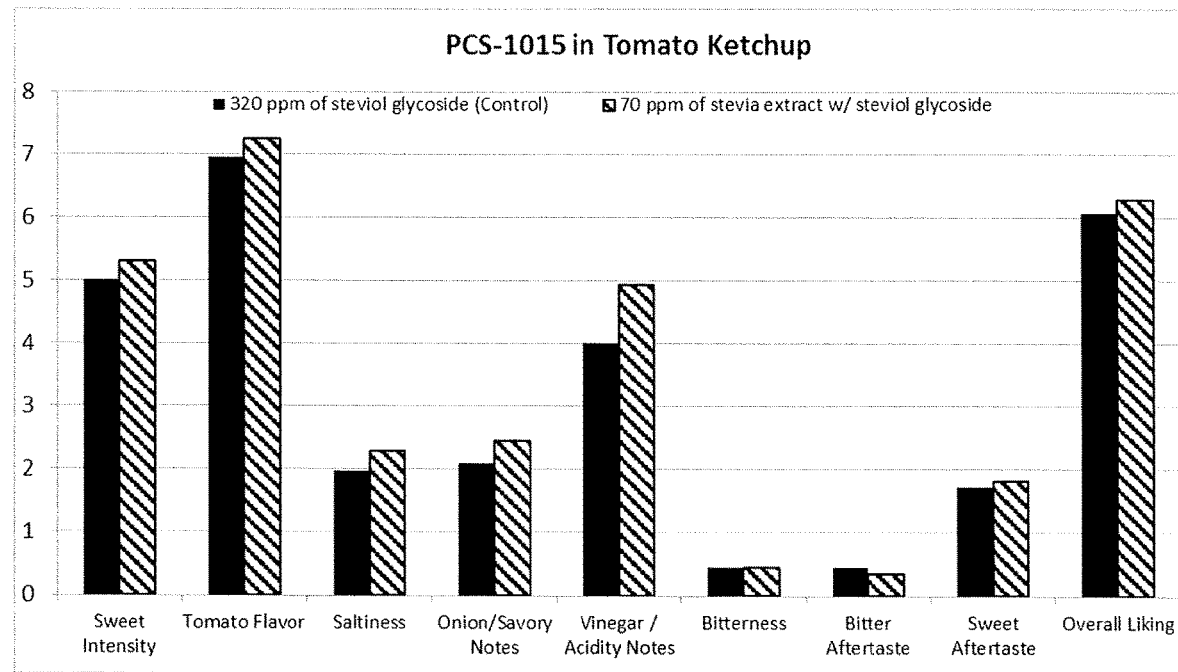

FIG. 6 shows the modification of flavor and sweetness profiles caused by the addition of stevia extract (PCS-1015). The results indicate the test samples containing stevia extract, PCS-1015, had a significant increase in herbal notes, and savory (onion/garlic) notes at a 95% confidence interval. The test sample containing PCS-1015 had directionally lower bitterness, bitter aftertaste and overall liking at a 90% confidence interval compared to the control sample.

Example 6

Effect of PCS-1015 (Stevia Extract) on Flavor Modification of Dairy Applications A chocolate flavored dairy beverage was developed to determine the flavor modification effect of stevia extract (PCS-1015) in dairy beverage. The panel evaluated samples of chocolate milk for overall acceptance and attribute intensities (chocolate flavor, dairy notes, sweetness, bitterness and aftertaste). The two samples (Table 12) included: 1) 50% sugar reduced control sample containing stevia glycosides, and 2) 50% reduced sugar test sample containing stevia glycoside and 80 ppm of stevia extract, PCS-1015.

TABLE 12

Effect of PCS-1015 (stevia extract) on flavored dairy beverage

| Dairy Formula | 50% Total Sugar Reduction with steviol glycoside | 50% Total Sugar Reduction with stevia extract and stevia glycoside |
| --- | --- | --- |
| 2% Reduced fat Milk | 96.5803 | 96.5753 |
| Sugar | 2.40 | 2.40 |
| Cocoa Powder | 0.80 | 0.80 |
| Palsgaard 150 ChoMilk | 0.20 | 0.20 |
| Steviol Glycosides | 0.0197 | 0.0197 |
| PCS-1015 |  | 0.080 |
| Total | 100 | 100 |

TABLE 13

Sensory evaluation of Dairy beverage

| | |
| --- | --- |
| Nature of Participants: | Company employees |
| Number of Sessions | 1 |
| Number of Participants: | 30 |
| Test Design: | Balanced, randomized within pair. Blind |
| Sensory Test Method: | Intensity and acceptance ratings |
| Environmental Condition | Standard booth lighting |
| Attributes and Scales: | Overall Acceptance on a 10-pt hedonic scale where 10 = Extremely Like and 0 = Extremely Dislike Overall Liking, sweetness, bitterness, dairy notes, chocolate, and Aftertaste. 10-pt continuous intensity scale where 0 = Imperceptible and 10 = Extremely Pronounced |
| Statistical Analysis: | ANOVA (by Block) with Post Hoc Duncan's Test |
| Sample Size | ~1.5 oz. in a clear capped plastic cup |
| Serving Temperature | Refrigerated temperature (~45° F.) |
| Serving/Panelists Instruction: | Samples served simultaneously. Panelists instructed to read ingredient statement, evaluate each sample. |

Figure 7:
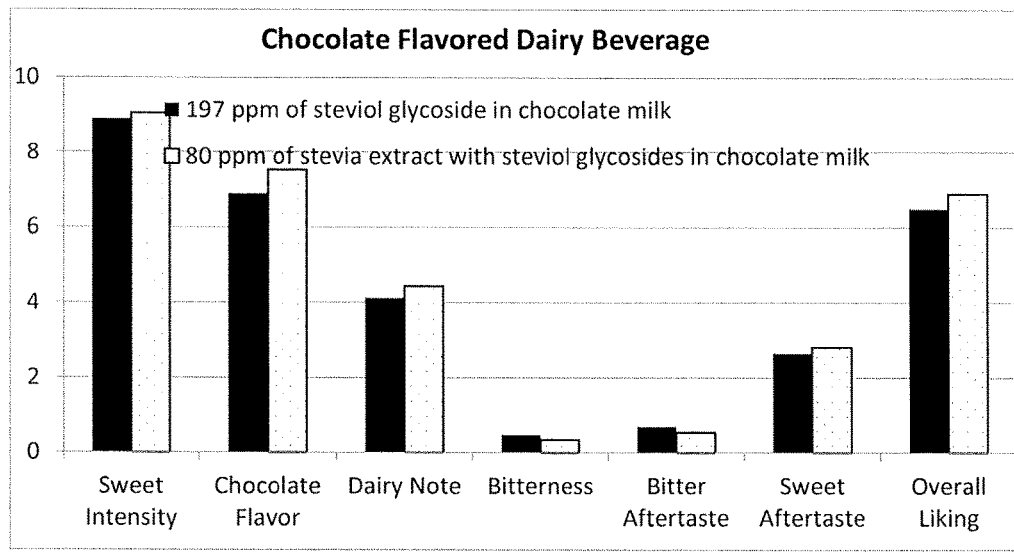

FIG. 7 shows the modification of flavor and sweetness profiles caused by the addition of stevia extract (PCS-1015). The results indicate the 50% sugar reduced sample containing steviol glycoside sweetener and stevia extract, PCS-1015, had significantly higher chocolate flavor.

Example 7

Effect of Stevia Extract (PCS-5001) on Flavor Modification of Baked Goods Applications A lemon poppy seed flavored muffin formulation was developed to determine the flavor modification effect of stevia extract (PCS-5001) in baked good applications. To test the contribution of PCS-5001 in baked goods, lemon flavored poppy seed muffins were baked with a 45% sugar reduced formulation with steviol glycoside as control, and sugar reduced formulation with steviol glycoside and stevia extract (PCS-5001) as a test sample as shown in Table 14. A thirty member consumer panel evaluated two samples of lemon poppy seed muffins for several attributes (lemon, vanilla flavors, brown notes, sweet & bitter aftertaste).

TABLE 14

Effect of PCS-5001 (stevia extract) on baked goods

| Ingredients | Steviol Glycoside (400 ppm) Control | Steviol glycoside w/120 ppm stevia extract |
|---|---|---|
| DRY Ingredients | | |
| Sucrose | 12.3722 | 12.3682 |
| All Purpose Flour | 17.6434 | 17.6434 |
| Whole Wheat Flour | 5.8763 | 5.8763 |
| Poppy Seeds | 1.0648 | 1.0648 |
| Maltodextrin - 10DE | 2.1368 | 2.1368 |
| Fibersol2 (ADM/Matsutani) | 1.0648 | 1.0648 |
| Modified Starch - Inscosity 656 | 1.0648 | 1.0648 |
| Lemon Flavor - Firmenich | 0.8860 | 0.8860 |
| Salt (Sodium Chloride) | 0.7479 | 0.7479 |
| Baking Powder | 1.0648 | 1.0648 |
| Baking Soda | 0.3205 | 0.3205 |
| Steviol Glycoside | 0.0400 | 0.0400 |
| Stevia extract (PCS-5001) | | 0.0120 |
| Wet Ingredients | | |
| Milk, 2% | 27.2444 | 27.2444 |
| Soybean Oil | 11.7525 | 11.7525 |
| Whole Eggs | 8.5473 | 8.5473 |
| Water | 5.3420 | 5.3420 |
| Yogurt, Plain Nonfat | 1.6026 | 1.6026 |
| Lemon Juice, 100% | 0.6410 | 0.6410 |
| Vanilla Extract | 0.5342 | 0.5342 |
| | 100 | 100 |

Figure 8:
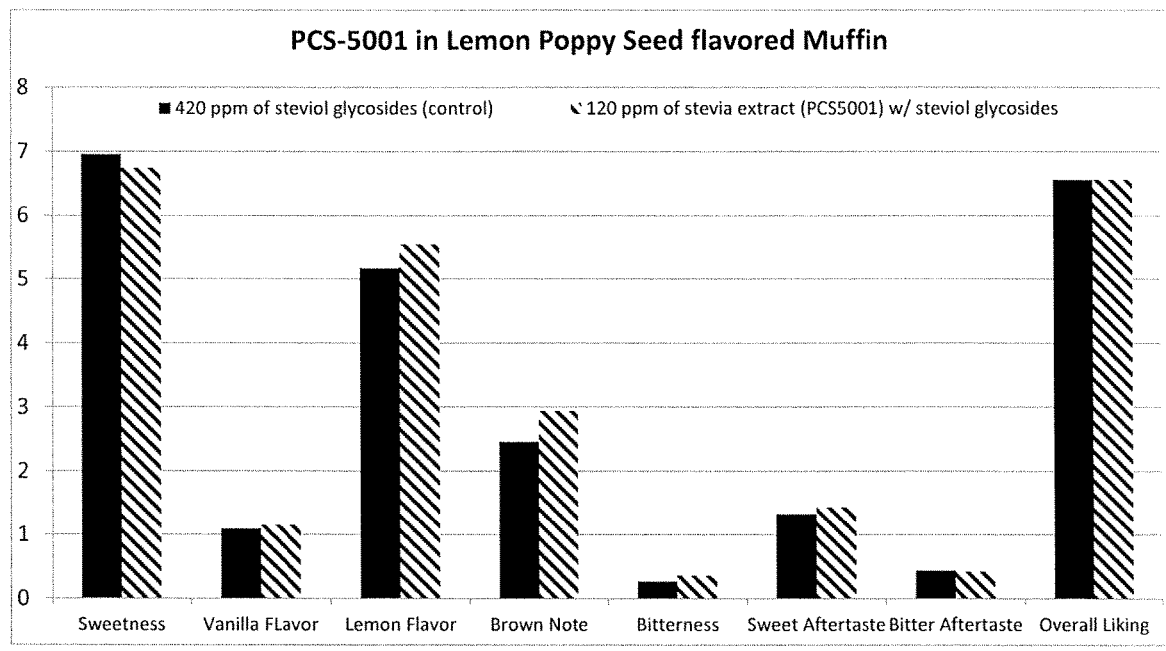

FIG. 8 shows the modification of flavor and sweetness profiles caused by the addition of stevia extract (PCS-5001). The panel found that the addition of stevia extract provided an increase in brown note than control sample without stevia extract (at 90% confidence).

Example 8

Effect of Stevia Extract (PCS-5001) on Flavor Modification of Reduced Sodium Applications A 30% salt reduced tortilla chip formulation was developed to determine the flavor modification effect of stevia extract (PCS-5001) in a salt reduced applications. To test the contribution of PCS-5001 in a salt reduced application, cheddar cheese flavor tortilla chips were coated with a control salt formulation, and a 30% salt reduced formulation with stevia extract (PCS-5001) as a test sample as shown in Table 15. A sixteen member consumer panel evaluated two samples of cheddar cheese flavored tortilla chips for different attributes (sweet intensity, saltiness, cheese flavor, dairy notes, corn flavor, bitterness, and sweet & bitter aftertaste).

Figure 9:
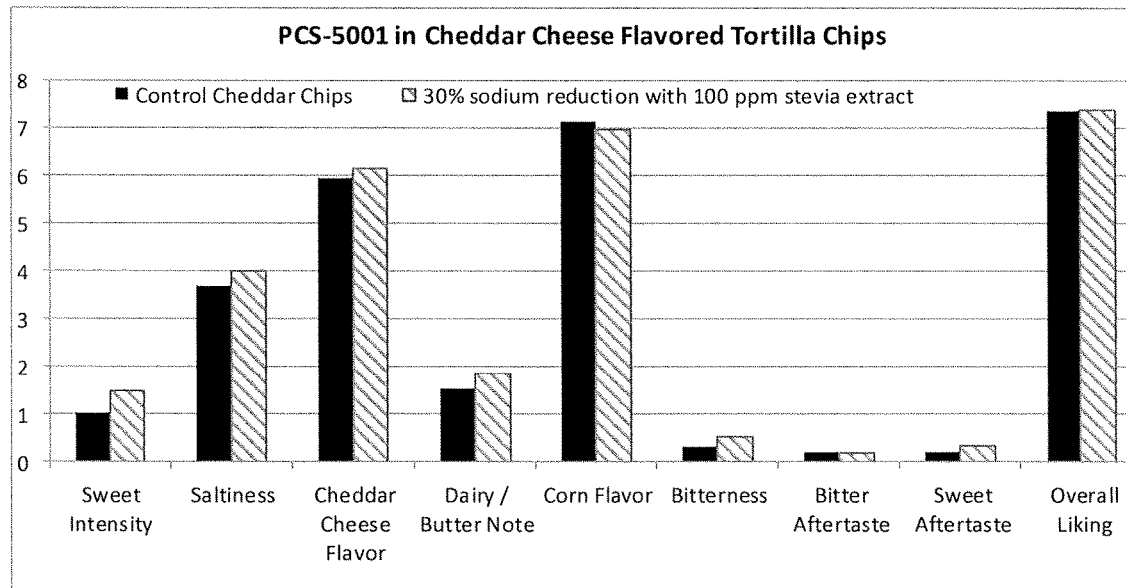

FIG. 9 shows the modification of flavor and salt perception caused by the addition of stevia extract (PCS-5001). The panel found the addition of stevia extract in a 30% salt reduced formulation provided an increase in salt perception, parity to the full sodium control. In addition, stevia extract provided an increase in sweet intensity and dairy note higher than control sample without stevia extract (at 95% confidence).

TABLE 15

Tortilla Chips with Cheddar Cheese 30% less sodium

| | Control | 30% Less Salt |
|---|---|---|
| Corn chips | 78 | 78.33 |
| Cheese seasoning | 10 | 10.04 |
| Vegetable Oil | 11 | 11.05 |
| Added Salt | 1 | 0.57 |
| PCS-5001 | | 0.01 |
| Total w (g) | 100 | 100.00 |

Example 9

Effect of Stevia Extract (PCS-5001) on Flavor Modification of Dried Meat Applications A beef jerky formulation was developed to determine the flavor modification effect of stevia extract (PCS-5001) in a dried meat applications. To test the contribution of PCS-5001 in a dried meat application, flank steak was marinated with a reduced sugar control formulation, and a 30% sugar reduced formulation with steviol glycosides and stevia extract (PCS-5001) as a test sample as shown in Table 16. A twenty member consumer panel evaluated two samples of beef jerky for different attributes (sweet intensity, saltiness, black pepper, teriyaki flavor, fat-like intensity, beef flavor and sweet aftertaste).

Figure 10:
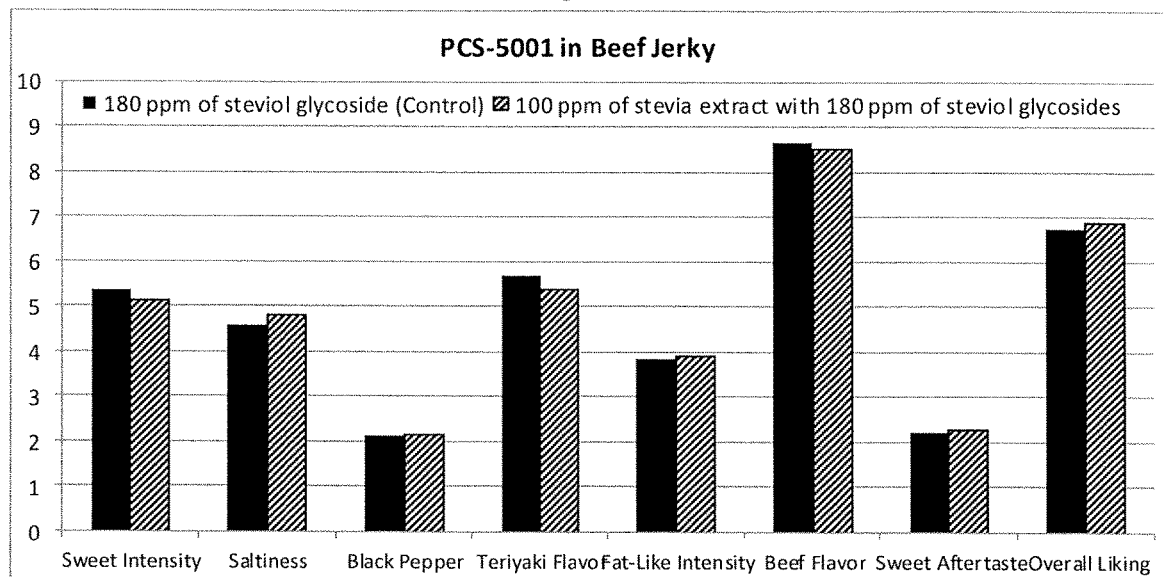

FIG. 10 shows the modification of flavor and salt perception caused by the addition of stevia extract (PCS-5001). The panel found the addition of stevia extract in a 30% sugar reduced formulation provided an increase in salt perception.

TABLE 16

30% sugar reduced Beef Jerky

| | Control (%) | Stevia Extract |
|---|---|---|
| Flank Steak | 75.44 | 75.44 |
| Balsamic vinegar | 10.15 | 10.15 |
| Salt | 2.46 | 2.46 |
| Pepper | 0.83 | 0.83 |
| Sugar | 6.88 | 6.88 |
| Liquid smoke Water | 0.86 | 0.86 |
| Garlic powder | 0.44 | 0.44 |
| Onion powder | 0.44 | 0.44 |
| Steviol Glycoside | 0.018 | 0.018 |
| PCS-5001 (stevia extract) | | 0.0100 |
| Worcestershire sauce | 2.46 | 2.46 |
| | 100 | 100 |

Example 10

Effect of Stevia Extract (PCS-5001) on Flavor Modification of Reduced Sodium Applications in Brown Gravy A 30% sodium reduced brown gravy formulation was developed to determine the flavor modification effect of stevia extract (PCS-5001) in a salt reduced applications. To test the contribution of PCS-5001 in a salt reduced application, a 30% sodium reduced brown gravy formulation, and a 30% salt reduced formulation with stevia extract (PCS-5001) as a test sample. A thirty member consumer panel evaluated two samples of brown gravy for different attributes (sweet intensity, saltiness, black pepper, beef flavor, and onion/savory notes, bitterness, and sweet & bitter aftertaste).

Figure 11:
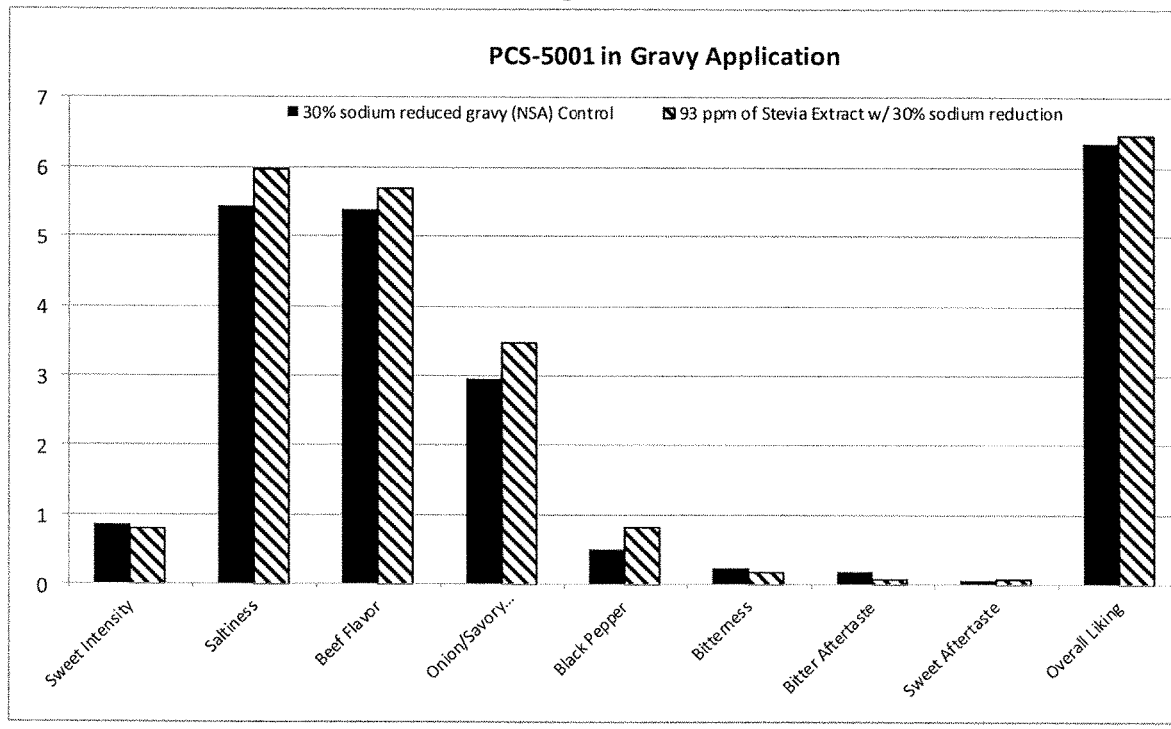

FIG. 11 shows the modification of flavor and salt perception caused by the addition of stevia extract (PCS-5001). The panel found the addition of stevia extract in a 30% salt reduced formulation provided an increase in salt perception compared to 30% sodium reduced control. In addition, stevia extract provided an increase in savory and black pepper note higher than control sample without stevia extract (at 95% confidence). There was also a decrease in bitter aftertaste.

Example 11

Effect of Stevia Extract on Flavor Modification of Dairy Product

To evaluate the contribution of PCS-1015 (MLD-1), a stevia extract, to a dairy product, two 50% reduced sugar chocolate milk samples were prepared and tested by a consumer panel of 30 company employees. The consumer panel evaluated those two samples of chocolate milk for overall acceptance and attribute intensities (chocolate flavor, dairy notes, sweetness, bitterness and aftertaste) in two sessions. In session one, the two samples included: 1) a 50% sugar reduced control sample containing PureCircle Alpha (steviol glycoside sweetener) and 2) 50% sugar reduced test sample containing PureCircle Alpha and 70 ppm PCS-1015 (MLD-1). In session two, the two samples included: 1) a 50% sugar reduced control sample containing PureCircle Alpha (steviol glycoside sweetener) and 2) 50% sugar reduced test sample containing PureCircle Alpha and 80 ppm PCS-1015 (MLD-1). Tables 17 shows the formula of the control and test samples of 50% reduced sugar.

TABLE 17

50% sugar reduced Chocolate Milk with PCS-1015

| Dairy Formula | 50% Total Sugar Reduction with PureCircle Alpha | 50% Total Sugar Reduction with PC Alpha & PCS-1015 | 50% Total Sugar Reduction with PC Alpha & PCS-1015 |
|---|---|---|---|
| 2% Reduced fat Milk | 96.5803 | 96.5743 | 96.5753 |
| Sugar | 2.40 | 2.40 | 2.40 |
| Cocoa Powder 10/12 | 0.80 | 0.80 | 0.80 |
| Palsgaard 150 ChoMilk | 0.20 | 0.20 | 0.20 |
| PureCircle Alpha | 0.0197 | 0.0197 | 0.0197 |
| PCS-1015 (MLD-1) | | 0.0070 | 0.0080 |
| Total | 100 | 100 | 100 |

Figure 12:
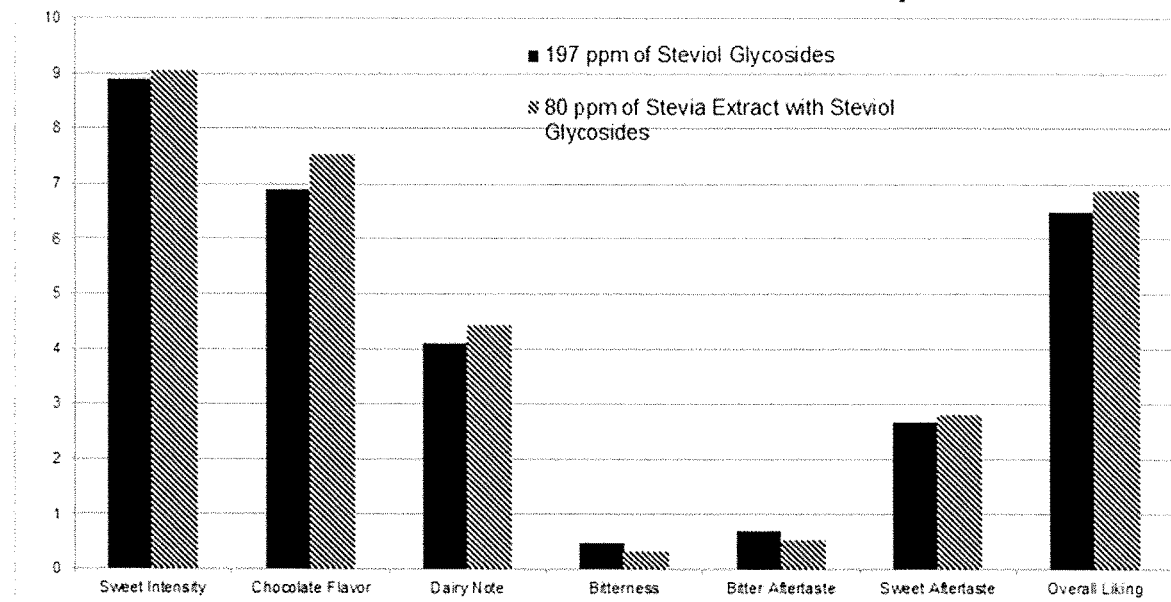

Table 18 shows the sensory results with the two test samples. Both test samples showed the impact of the stevia extract (PCS 1015) on the Chocolate flavor notes and dairy note. At 80 ppm use level, the chocolate milk sample showed better sweetness profile and overall liking than the control sample. FIG. 12 shows the comparison of the taste profile between the control and the test sample with 80 ppm stevia extract PCS 1015.

TABLE 18

Summary of the overall acceptance and mean attribute intensity results for each reduced sugar chocolate milk samples tested by 30 panel members.

Summary of Mean-Scores, P-Values, and Significance Test Result Code - chocolate milk with 70 ppm MLD-1

| Attribute | 197 ppm of Alpha Only (Control) | 70 ppm of MLD-1 w/ PC Alpha | P-Value | Sig |
|---|---|---|---|---|
| Sweet Intensity | 8.85 | 8.89 | 0.8555 | NS |
| Chocolate Flavor | 6.82 b | 7.70 a | 0.0482 | *** |
| Dairy Note | 3.61 b | 4.19 a | 0.1934 | * |
| Bitterness | 0.84 | 0.83 | 0.9500 | NS |
| Bitter Aftertaste | 0.74 | 0.70 | 0.6096 | NS |
| Sweet Aftertaste | 3.02 | 3.15 | 0.7232 | NS |
| Overall Liking | 7.12 | 7.42 | 0.5114 | NS |

Summary of Mean-Scores, P-Values, and Significance Test Result Code - chocolate milk with 80 ppm MLD1

| Attribute | 197 ppm of Alpha Only (Control) | 80 ppm of MLD-1 w/ PC Alpha | P-Value | Sig |
|---|---|---|---|---|
| Sweet Intensity | 8.90 b | 9.05 a | 0.1557 | * |
| Chocolate Flavor | 6.89 b | 7.53 a | 0.0048 | *** |
| Dairy Note | 4.12 b | 4.44 a | 0.1470 | * |
| Bitterness | 0.49 | 0.35 | 0.2473 | NS |
| Bitter Aftertaste | 0.71 a | 0.55 b | 0.1824 | * |
| Sweet Aftertaste | 2.66 | 2.82 | 0.5177 | NS |
| Overall Liking | 6.49 b | 6.89 a | 0.1908 | * |

\* = 80% CI,
\*\* = 90% CI,
\*\*\* = 95% CI

Example 12

Effect of Stevia Extract on Desserts (Vanilla Custard)

To test the contribution of the stevia extract, PCS-1015 in gelatin and puddings, two 30% calorie reduced vanilla custard samples were tested: 1) sweetened with PureCircle Alpha, a PureCircle *stevia* sweetener, 2) sweetened with PureCircle Alpha and PCS-1015 (MLD-1). Table 19 shows the formulation of the control and test samples. A panel of 30 trained panelists with extensive experience in profiling sensory attributes tasted both samples.

To prepare the sample, blend the PureCircle Alpha and the test ingredient (PCS-1015) with the dry ingredients. Add the dry ingredients to the milk using good agitation. Heat on low until all ingredients are dissolved. Heat up to 95° C. for 10 minutes to cook up the starches. Add flavors, stir it, cool, stir it before place it in the refrigerator. Serve at chilled in 1 oz cups.

TABLE 19

Reduced sugar dessert (Vanilla Custard) with PCS-1015

| | Control with PureCircle Alpha | Test with PureCircle Alpha w/ *stevia* extract |
|---|---|---|
| Milk (1% fat) | 94.27 | 94.27 |
| Sucrose | 4.00 | 4.00 |
| Starch Perma Flo Tate & Lyle | 1.25 | 1.25 |
| TIC Carrageenan | 0.09 | 0.09 |
| Salt | 0.06 | 0.06 |

TABLE 19-continued

Reduced sugar dessert (Vanilla Custard) with PCS-1015

|  | Control with PureCircle Alpha | Test with PureCircle Alpha w/ stevia extract |
|---|---|---|
| ROHA Beta Carotene | 0.05 | 0.05 |
| French Vanilla Flavor UV 420-066-7 | 0.15 | 0.15 |
| Steviol Glycoside | 0.0166 | 0.0166 |
| Stevia Extract | — | 0.0080 |
| Total | 100 | 100 |

Figure 13:
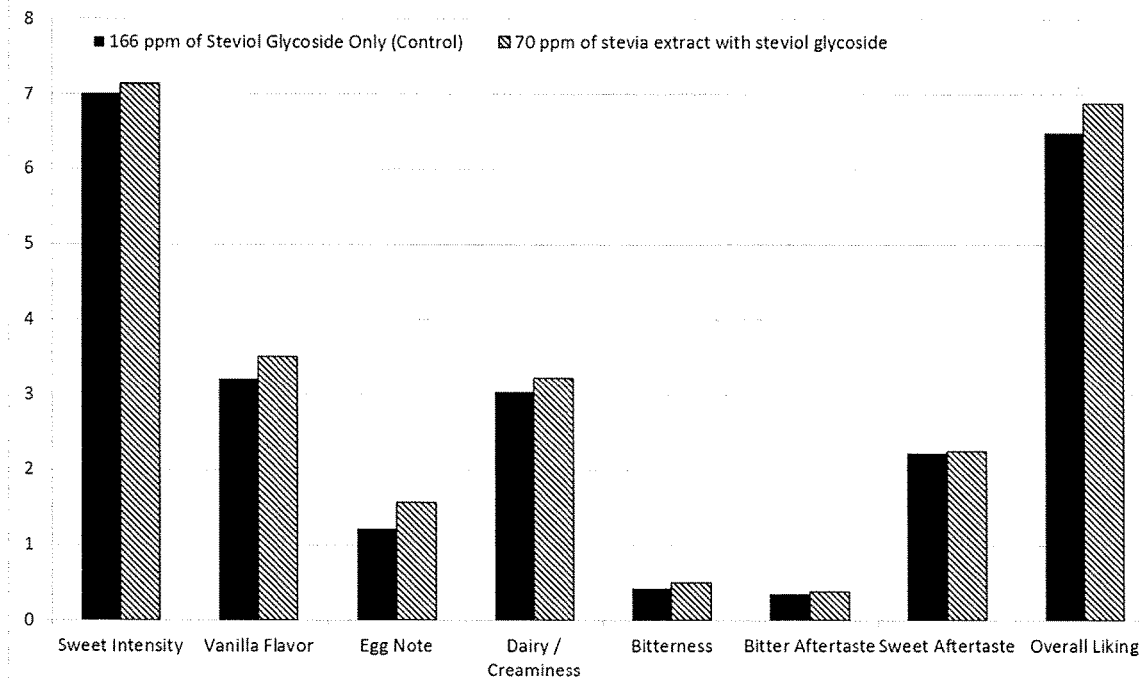

The trained panel found that the test sample had stronger sweet intensity, vanilla, dairy flavor notes and overall liking at 80% confidence. The sample containing stevia extract also had significantly higher egg note at 95% confidence. FIG. 13 shows the pictorial rendition of the sensory difference between the control and test dessert samples

TABLE 20

Summary of the overall acceptance and mean attribute intensity results for reduced sugar dessert (Vanilla Custard) with PCS-1015

| Attribute | 166 ppm of Alpha Only (Control) | 70 ppm of MLD-1 with Alpha | P-Value | Sig |
|---|---|---|---|---|
| Sweet Intensity | 7.01 a | 7.13 b | 0.1095 | * |
| Vanilla Flavor | 3.22 a | 3.5 b | 0.1299 | * |
| Egg Note | 1.22 a | 1.56 b | 0.0497 | *** |
| Dairy/Creaminess | 3.04 a | 3.22 b | 0.1164 | * |
| Bitterness | 0.43 | 0.5 | 0.3001 | NS |
| Bitter Aftertaste | 0.36 | 0.38 | 0.7692 | NS |
| Sweet Aftertaste | 2.23 | 2.24 | 0.8794 | NS |
| Overall Liking | 6.49 a | 6.87 b | 0.1149 | * |

Although various embodiments of the present invention have been disclosed here for purposes of illustration, it should be understood that a variety of changes, modifications and substitutions may be incorporated without departing from either the spirit or the scope of the invention.

What is claimed is:

1. A flavor modifying composition comprising from about 45% to about 65% by weight total steviol glycosides (TSG), and from about 35% to about 50% by weight other glycosylated diterpene derivative plant molecules;
   wherein the total steviol glycosides comprise 5% to 20% by weight Rebaudioside A, less than 5% by weight Rebaudioside B, and 2% to 15% by weight Stevioside;
   wherein the other glycosylated diterpene derivative plant molecules comprise one or more selected from the group consisting of: 13-[(2-O-(6-O-β-D-glucopyranosyl)-β-D-glucopyranosyl-β-D-glucopyranosyl)oxy] kaur-16-en-18-oic acid β-D-glucopyranosyl ester; 13-[(2-O-β-D-glucopyranosyl-3-O-β-D-fructofuranosyl-β-D-glucopyranosyl) oxy] kaur-16-en-18-oic acid β-D-glucopyranosyl ester, and combinations thereof;
   and wherein the composition, when used below its sweetness recognition threshold level, reduces bitterness and bitter aftertaste as compared to a control composition that does not contain the flavor modifying composition.

2. The flavor modifying composition of claim 1, wherein the total steviol glycosides further include minor steviol glycosides selected from the group consisting of Reb E, Reb N, and Reb O; wherein the content of each of these minor steviol glycosides is less than 10% by weight of the composition.

3. The flavor modifying composition of claim 1, wherein the total steviol glycosides further include one or more additional steviol glycosides selected from the group consisting of Steviolbioside, Rubusoside, Dulcoside A, and Reb F; wherein the content of each of these additional steviol glycosides is less than 5% by weight of the composition.

4. A food, beverage, medical food, or pharmaceutical product comprising the flavor modifying composition of claim 1, wherein the food, beverage, medical food, or pharmaceutical product has reduced bitterness and bitter aftertaste as compared to a control product made without the flavor modifying composition of claim 1.

5. The food and beverage product of claim 4, wherein the flavor modifying composition is present at concentrations ranging between 1 to 1000 ppm to provide flavor modification below the sweetness recognition threshold of the flavor modifying composition.

6. The food and beverage product of claim 4, wherein the flavor modifying composition is present at concentrations ranging from 5 to 250 ppm to provide flavor modification below the sweetness recognition threshold of the flavor modifying composition.

7. The food or beverage product of claim 4, selected from the group consisting of: a carbonated soft drink, a fruit juice, an alcoholic beverage, a dairy food, a dairy beverage, a dessert, a baked good, a cereal product, a confectioner, a sauce, a gravy, a dressing, a meat product, a seasoning & condiment, a snack product and a table top sweetener.

8. A method of increasing a taste and flavor intensity of a food or beverage product, comprising the step of adding the taste and flavor modifying composition of claim 1 to a food or beverage product.

9. A method of improving a salt perception and reducing a sodium content of a food or beverage product, comprising a seasoning, a meat product, a snack product, a sauce or a gravy, comprising the step of adding the taste and flavor modifying composition of claim 1 to said food or beverage product.

10. The method of claim 9, wherein a savory taste and flavor profile is improved with more salty taste than a comparative taste and flavor profile of a comparative product which does not include the taste and flavor modifying composition.

* * * * *